United States Patent [19]
Bushey et al.

[11] 4,405,632
[45] Sep. 20, 1983

[54] NOVEL DERIVATIVES OF BICYCLIC 2-IMINOTHIAZOLIDINE OXIMES

[75] Inventors: Dean F. Bushey; Themistocles D. J. D'Silva, both of South Charleston, W. Va.

[73] Assignee: Union Carbide Corporation, Danbury, Conn.

[21] Appl. No.: 163,496

[22] Filed: Jun. 27, 1980

[51] Int. Cl.³ .................. A61K 31/41; C07D 491/00; C07D 487/00; C07D 241/36
[52] U.S. Cl. .................................. 424/270; 548/153; 548/154; 544/278; 544/344
[58] Field of Search ............... 548/153, 154; 424/270; 544/344, 278

[56] References Cited
U.S. PATENT DOCUMENTS 3,717,690  2/1973  Newman .................................. 71/86
3,860,578  1/1975  Lee ................................ 260/239 BF
3,957,990  5/1976  Booth et al. ........................ 424/251

OTHER PUBLICATIONS

Dornow, A. et al., Chem. Ber., 99, 72 (1966).

Primary Examiner—Donald G. Daus
Assistant Examiner—S. A. Gibson
Attorney, Agent, or Firm—R. C. Brown; C. J. Vicari; W. R. Moran

[57] ABSTRACT

Novel derivatives of bicyclic 2-iminothiazolidine oximes and methods of preparing same. This invention is also directed to an insecticidal composition comprising an acceptable carrier and an insecticidally effective amount of a compound of this invention, as well as to a method of controlling insects which comprises subjecting the insects to an insecticidally effective amount of a compound of this invention.

27 Claims, No Drawings

NOVEL DERIVATIVES OF BICYCLIC 2-IMINOTHIAZOLIDINE OXIMES

This invention relates to novel derivatives of bicyclic 2-iminothiazolidine oximes and methods of preparing same. This invention is also directed to an insecticidal composition comprising an acceptable carrier and an insecticidally effective amount of a compound of this invention, as well as to a method of controlling insects which comprises subjecting the insects to an insecticidally effective amount of a compound of this invention.

More particularly, this invention relates to compounds of the formula:

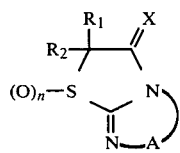

wherein $R_1$ and $R_2$ are the same or different and are individually hydrogen, $C_1$–$C_6$ alkyl or halogen;

n=0, 1 or 2;

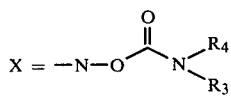

including E and Z isomers;

A is an acyclic, cyclic, or bicyclic alkylene or alkenylene group, or an ortho-substituted phenylene group which forms an unsaturated five, six or seven membered heterocyclic ring which can also contain oxygen, sulfur, nitrogen, or carbonyl in addition to the two nitrogens, said alkylene, alkenylene, or phenylene ring systems being optionally substituted with one or more $C_1$–$C_4$ alkyl, cyclohexyl, alkoxy, phenoxy, alkylthio, halogen, amido, alkylamido, nitrile, acyl, or nitro groups;

$R_3$ and $R_4$ may be the same or different and are individually hydrogen, $C_1$–$C_4$ alkyl or $C_1$–$C_4$ alkanoyl which can be substituted with one or more halogens and in the case when $R_3$ is alkyl $R_4$ can also be —(S)$_y$—$R_5$ wherein:

y=1 or 2;

$R_5$=(a) $C_1$–$C_{18}$ alkyl, $C_3$–$C_8$ cycloalkyl or perhaloalkyl;

(b) dialkyl amino, piperidino, pyrrolidino, or a morpholino group each of which may be unsubstituted or substituted with one or two alkyl groups; or (c) a phenyl group which may be unsubstituted or substituted with one or more alkyl, chloro, fluoro, cyano, nitro, alkoxy, trifluoromethyl, alkylthio, alkylsulfinyl, alkylsulfonyl, alkoxy alkyl, alkylthioalkyl, alkylsulfinylalkyl, alkylsulfonylalkyl, or dialkylamino; or (d) a group of the formula:

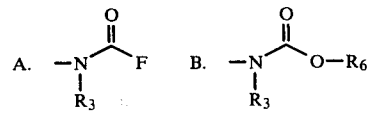

wherein:

$R_6$ is:

(1) $C_1$–$C_{12}$ alkyl, alkoxyalkyl, or a phenylalkyl group; or (2) a phenyl group which may be unsubstituted or substituted with one or more $C_1$–$C_{12}$ alkyl, chloro, fluoro, alkoxy, alkylthio, alkylthioalkyl, alkylsulfinyl, alkylsulfinylalkyl, alkylsulfonyl, alkylsulfonylalkyl, alkynyloxy, dialkylamino, alkoxyimino, formamidino, cyano, dioxolanyl, or dithiolanyl groups in any combination; or (3) a naphthyl, tetrahydronaphthyl, dihydrobenzofuranyl, benzodioxolanyl, or benzothienyl group all of which may be unsubstituted or substituted with one or more alkyl groups; or (4) a group of the formula

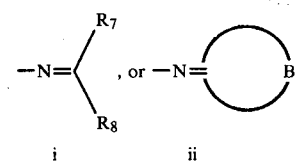

wherein:

$R_7$ is chloro, alkyl, alkoxy, alkylthio, cyanoalkylthio, amidoalkylthio or cyano group; or $R_7$ is hydrogen provided $R_8$ is not hydrogen;

$R_8$ is an alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, haloalkyl, or phenyl group; said phenyl group may contain one or more alkyl, chloro, or fluoro groups in any combination; or $R_8$ is hydrogen provided $R_7$ is not hydrogen;

B is a divalent aliphatic chain completing a five or six membered heterocyclic ring structure, said aliphatic chain having from 2 to 24 aliphatic carbon atoms, said ring structure may include in any combination one, two or three divalent oxygen, sulfur, sulfinyl, or sulfonyl groups and may further include one group selected from a divalent amino group, a $C_1$–$C_8$ divalent alkylamino group, or a divalent carbonyl group;

with the proviso that when $R_6$ is a phenyl group substituted with an alkyl group, no single alkyl or alkylene moiety in any $R_5$, $R_6$, $R_7$, or $R_8$ group can include more than eight carbon atoms except where indicated.

In general, the insecticidal compounds of this invention can be prepared by a variety of methods. The methods are illustrated by the reaction schemes set forth below.

Method I

-continued

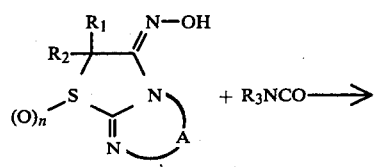 + R₃NCO ⟶

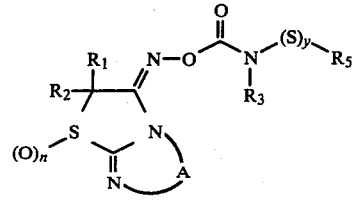

Method V

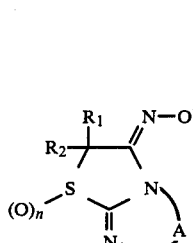

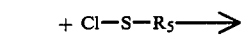 + Cl—S—R₅ ⟶

Method II

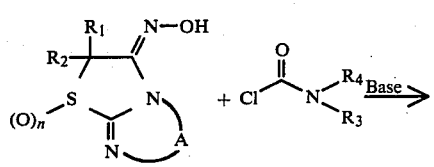

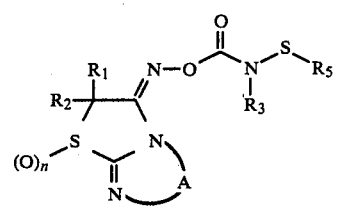

Method III

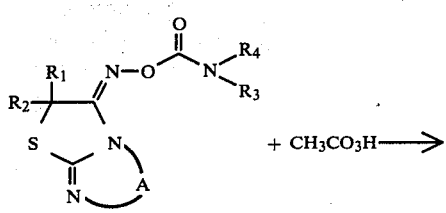
+ CH₃CO₃H ⟶

In the above reactions methods, the value of the letter constituents are as indicated previously.

The reactions illustrated in Methods I to V are conducted in inert solvents. Any inert solvent such as methylene chloride, chloroform, acetonitrile, benzene, toluene, xylene, dioxane, tetrahydrofuran or a mixture of these solvents can be used in these reactions. Preferably these reactions are conducted in methylene chloride or methylene chloride/acetonitrile, depending on solubility characteristics of the starting oxime.

Reaction temperatures are not critical and can be varied over a wide range depending to a large extent on solubility of the reactants. The reactions are preferably conducted at a temperature of −10° to 50° C. Reaction pressures are not critical. For convenience these reactions are usually conducted at atmospheric or autogeneous pressure.

The reaction illustrated in Method I is preferably conducted in the presence of a quantity of a catalyst sufficient to provide a suitable and reasonable rate. In general, any conventional catalyst of the type commonly employed to promote reactions between isocyanate compounds and compounds that contain an active hydrogen can be used. Preferred catalysts are tertiary amines such as triethylamine, trimethylamine, pyridine or the like and dibutyltin diacetate.

The reaction illustrated in Method II is conducted in the presence of one equivalent of a base such as triethylamine, trimethylamine, pyridine, potassium hydroxide or the like. When an inorganic base is used phase transfer agents may be used to facilitate the transfer of the base across the organic/inorganic phase interface. Illustrative of useful phase transfer agents are crown ether compounds, quaternary ammonium halide compounds or the like. The chloro compound starting reactant is Method IV

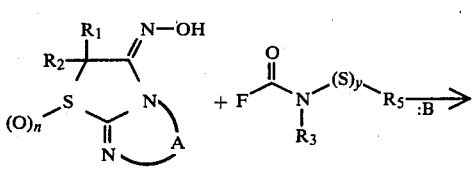

commercially available or easily prepared from known procedures.

The reaction illustrated in Method III is an oxidation reaction of the product of Method II. The peracetic acid is admixed with the starting reactant and stirred in ethyl acetate at room temperature until the product is produced.

The reaction illustrated in Method IV is conducted in the presence of an acid acceptor. The molar ratio of acid acceptor to either reactant is usually unity although a slight excess of acid acceptor may be employed, if desired. The acid acceptor utilized in the conduct of the reaction of Method V may be either an organic or inorganic base. Aromatic and aliphatic tertiary amines, such as triethylamine, pyridine, 1,4-diazobicyclo[2.2.2]octane and the like are representative of the organic bases. Bases such as sodium hydroxide, potassium carbonate or the like are illustrative of the inorganic bases which are useful in the conduct of this reaction.

When an inorganic base is used, phase transfer agents may be used to facilitate the transfer of the base across the organic/inorganic phase interface. Illustrative of useful phase transfer agents are crown ether compounds, quaternary ammonium halide compounds or the like.

The alkyl sulfenyl compounds of Method V are prepared by reacting the products of Method I with an alkyl sulfenylchloride in the presence of an organic or inorganic base. Aromatic and aliphatic tertiary amines, such as triethylamine, pyridine, 1,4-diazobicyclo[2.2.-2]octane and the like are representative of the organic bases. Bases such as sodium hydroxide, potassium hydroxide or the like are illustrative of the inorganic bases which are useful in the conduct of this reaction.

When an inorganic base is used, phase transfer agents may be used to facilitate the transfer of the base across the organic/inorganic phase interface. Illustrative of useful phase transfer agents are crown ether compounds, quaternary ammonium halide compounds, or the like.

In general, the 2-iminothiazolidine oximes used as starting materials for the novel compounds of this invention are disclosed in our copending application Ser. No. 163,631 which is filed concurrently herewith. For purpose of completeness, the disclosure of application Ser. No. 163,631 is incorporated herein by reference. Briefly however they can be conveniently prepared by reacting a cyclic thiourea with the dichloro-oxime as described below, in which $R_1$, $R_2$, and A are as described previously.

Method VI

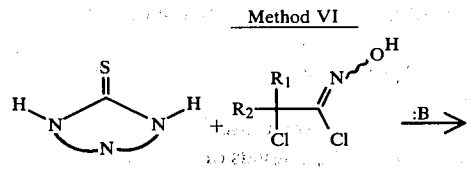

-continued
Method VI

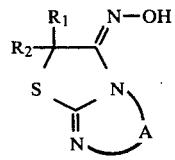

The reaction of Method VI can be conducted in aqueous or organic solvents with an appropriate acid acceptor. The acid acceptor in the conduct of the reaction of Method I may be either an organic or inorganic base. Aromatic and aliphatic tertiary amines, such as triethylamine, pyridine, 1,4-diazobicyclo[2.2.2]octane and the like are representative of the organic bases. Bases such as sodium hydroxide, potassium carbonate, sodium bicarbonate or the like are illustrative of the inorganic bases which are useful in the conduct of this reaction.

When an inorganic base is used, phase transfer agents may be used to facilitate the transfer of the base across the organic/inorganic phase interface. Illustrative of useful phase transfer agents are crown ether compounds, quaternary ammonium halide compounds or the like.

The reactions are preferably carried out in methanol using sodium bicarbonate as the acid acceptor. The temperature is preferably held between $-78°$ C. and $0°$ during addition of starting materials and the mixture is slowly allowed to warm to $25°$ C. The time of reaction varies between 16 hours and 3 days.

The 2-chlorohydroxamoyl chloride compounds of Method VI can be prepared by the method described in Ogloblin et al, J. Gen. Chem, USSR, 34, 1225 (1964).

The sulfenylated reactant of Method IV can be conveniently prepared by reacting hydrogen fluoride with an alkyl isocyanate to form the N-alkylcarbamoyl fluoride compound which is then reacted with an appropriate sulfenyl chloride, e.g. with sulfur dichloride ($SCl_2$) to form the bis-(N-alkyl-N-fluorocarbonylamino)sulfide. This particular material is then reacted with one equivalent of an appropriately substituted alcohol or oxime in the presence of an acid acceptor to form the corresponding mono-fluoro adduct. The carbamoyl fluorides are described in U.S. Pat. No. 4,091,016 and U.S. Pat. No. 3,639,471; Belgium Pat. Nos. 848,914 and 848,910; and German Offen. No. 2,813,374.

The thioureas used as reactants in Method VI are known materials which can be obtained from commercial sources or prepared in accordance with conventional methods known to those skilled in the art.

The following compounds are representative of compounds which can be used as precursors for the preparation of the novel compounds of this invention.

2,2-Dimethyl-3-hydroxyimino-[5,8]-methano-2,3,5,6,7,8-hexahydrothiazolo[3,2-a][1,3]diazepine;
2,2-Dimethyl-3-hydroxyimino-[5,8]-methano-2,3,5,8-tetrahydrothiazolo[3,2-a][1,3]diazepine;
2,2-Dimethyl-3-hydroxyimino-5-oxo-2,3,5,6,7,8-hexahydrothiazolo[3,2-a]benzimidazole;
2,2-Dimethyl-3-hydroxyimino-2,3,4,5,6,7-hexahydrothiazolo[3,2-c][1,3,5]thiadiazine;

2,2-Dimethyl-3-hydroxyimino-2,3-dihydro-9H-thiazolo[3,2-a]quinazoline;
5,6-Dichloro-2,2-dimethyl-3-hydroxyimino-2,3-dihydroimidazo[2,1-b]thiazole;
5,6-Dicyano-2,2-dimethyl-3-hydroxyimino-2,3-dihydroimidazo[2,1-b]thiazole;
2,2-Dimethyl-3-hydroxyimino-5-oxo-2,3-dihydro-5H-thiazolo[3,2-a]pyrimidine;
5,5-Dimethyl-6-hydroxyimino-2,3-dihydrothiazolo[3,2-d]tetrazole;
2,2-Dimethyl-3-hydroxyimino-2,3,4a,6,7,7a-hexahydro-5H-cyclopenta[4,5]imidazo[2,1-b]thiazole;
2,2-Dimethyl-3-hydroxyimino-2,3-dihydro-6H-thiazolo[3,2-b][1,2,4]oxadizole;
7,7-Dichloro-2,2-dimethyl-3-hydroxyimino-2,3-dihydrothiazolo[3,2-a]pyrimidine;
6,6-Dichloro-2,2-dimethyl-3-hydroxyimino-2,3,5,6-tetrahydro-7H-thiazolo[3,2-a]pyrimidine;
2,2-Dimethyl-3-hydroxyimino-5,7-dioxo-2,3-dihydro-5H,7H-thiazolo[3,2-c]oxadiazine;
2,2-Dimethyl-5-methoxy-3-hydroxyimino-2,3-dihydroimidazo[2,1-b]thiazole;
3-Hydroxyimino-2,3,5,6-tetrahydro-7H-thiazolo[3,2-a]pyrimidine;
2-Ethyl-3-hydroxylimino-2,3-dihydroimidazo[2,1-b]thiazole;
2-Trichloromethyl-3-hydroxyimino-2,3-dihydroimidazo[2,1-b]thiazole;
2-Isopropyl-3-hydroxyimino-2,3,5,6-tetrahydro-7H-thiazolo[3,2-a]pyrimidine; and
2,2-Dimethyl-3-hydroxyimino-2,3-dihydroimidazo[2,1-b]thiazole-1,1-dioxide.

The following insecticidally active compounds are representative of compounds which can be prepared from the precursor compounds by selecting appropriate starting materials for use in the procedures described above.

2,2-Dimethyl-3-[O-(methylcarbamoyl)oximino]-[5,8]-methano-2,3,5,6,7,8-hexahydrothiazolo[3,2-a][1,3]diazepine.
2,2-Dimethyl-3-[O-(methylcarbamoyl)oximino]-[5,8]-methano-2,3,5,8-tetrahydrothiazolo[3,2-a][1,3-diazepine.
2,2-Dimethyl-3-[O-(methylcarbamoyl)oximino]-5-oxo-2,3,5,6,7,8-hexahydrothiazolo[3,2-a]benzimidazole.
2,2-Dimethyl-3-[O-(methylcarbamoyl)oximino]-2,3,4,5,6,7-hexahydrothiazolo[3,2-c][1,3,5]thiadiazine.
2,2-Dimethyl-3-[O-(methylcarbamoyl)oximino]-2,3-dihydro-9H-thiazolo[3,2-a]quinazoline.
5,6-Dichloro-2,2-dimethyl-3-[O-(methylcarbamoyl)oximino]-2,3-dihydroimidazo[2,1-b]thiazole.
5,6-Dicyano-2,2-dimethyl-3-[O-(methylcarbamoyl)oximino]-2,3-dihydroimidazo[2,1-b]thiazole.
2,2-Dimethyl-3-[O-(methylcarbamoyl)oximino]-5-oxo-2,3-dihydro-5H-thiazolo[3,2-a]pyrimidine.
5,5-Dimethyl-6-[O-(methylcarbamoyl)oximino]-2,3-dihydrothiazolo[3,2-d]tetrazole.
2,2-Dimethyl-3-[O-(methylcarbamoyl)oximino]-2,3,4a,6,7,7a-hexahydro-5H-cyclopenta[4,5]imidazo[2,1-b]thiazole.
2,2-Dimethyl-3-[O-(methylcarbamoyl)oximino]-2,3-dihydro-6H-thiazolo[3,2-b][1,2,4]oxadiazole.
7,7-Dichloro-2,2-dimethyl-3-[O-(methylcarbamoyl)oximino]-2,3-dihydrothiazolo[3,2-a]pyrimidine.
6,6-Dichloro-2,2-dimethyl-3-[O-(methylcarbamoyl)oximino]-2,3,5,6-tetrahydro-7H-thiazolo[3,2-a]pyrimidine.
2,2-Dimethyl-3-[O-(methylcarbamoyl)oximino]-5,7-dioxo-2,3-dihydro-5H,7H-thiazolo[3,2-c]oxadiazine.
2,2-Dimethyl-5-methoxy-3-[O-(methylcarbamoyl)oximino]-2,3-dihydroimidazo[2,1-b]thiazole.
3-[O-(methylcarbamoyl)oximino]-2,3,5,6-tetrahydro-7H-thiazolo[3,2-a]pyrimidine.
2-Ethyl-3-[O-(methylcarbamoyl)oximino]-2,3 dihydroimidazo[2,1-b]thiazole.
2-Trichloromethyl-3-[O-(methylcarbamoyl)oximino]-2,3 dihydroimidazo[2,1-b]thiazole.
2-Isopropyl-3-[O-(methylcarbamoyl)oximino]-2,3,5,6-tetrahydro-7H-thiazolo[3,2-a]pyrimidine.
2,2-Dimethyl-3-[O-(methylcarbamoyl)oximino]-2,3-dihydroimidazo[2,1-b]thiazole-1,1-dioxide.
2,2-Dimethyl-2,3,5,6-tetrahydro-7H-3-[[O-[N-methyl-N-(N'-methyl-N'-((2-methyl-2-(methylthio)propylidene)aminooxycarbonyl) aminosulfenyl) carbamoyl]oximino]]thiazolo[3,2-a]pyrimidine.
2,2-Dimethyl-2,3 dihydro-3[[O-[N-methyl-N-(N'-methyl-N'-(2,3-dihydro-2,2-dimethylbenzofuran-7-oxocarbonyl)aminosulfenyl)carbamoyl]oximino]-]imidazo[2,1-b]thiazole.
2,2-Dimethyl-2,3-dihydro-3-[[O-[N-methyl-N-(N'-methyl-N'-((1-N,N-dimethylcarbamoyl-1-methylthio methylidene-aminooxycarbonyl)) aminosulfenyl)carbamoyl]oximino]]imidazo[2,1-b]thiazole.
2,2-Dimethyl-2,3,5,6-tetrahydro-7H-3[[O-[N-methyl-N-(N'-methyl-N'-(1-N,N-dimethylcarbamoyl-2-methoxyiminopropylideneamino oxycarbonyl)aminosulfenyl) carbamoyl]oximino]]thiazole[3,2-a]pyrimidine.
2,2-Dimethyl-2,3-dihydro-3[[O-[N-methyl-N-(morpholinosulfenyl) carbamoyl]oximino]]imidazo[2,1-b]thiazole.
2,2-Dimethyl-2,3,5,6-tetrahydro-7H[[O-[N-methyl-N-(4-tert-butylphenyl sulfenyl)carbamoyl]oximino]]-thiazolo[3,2-a]pyrimidine.
2,2-Dimethyl-2,3-dihydro-3[[O-[N-methyl-N-(4-methylthio phenyl sulfenyl)carbamoyl]oximino]-]imidazo[2,1-b]thiazole.
2,2-Dimethyl-2,3,5,6-tetrahydro-7H-3[[O-[N-methyl-N-(N'-methyl-N'-((tert-butoxycarbonyl))amino sulfenyl)carbamoyl]oximino]]thiazolo[3,2-a]pyrimidine.
2,2-Dimethyl-2,3-dihydro-3-[[O-[N-methyl-N-(tert-butylthiosulfenyl) carbamoyl]oximino]]imidazo[2,1-b]thiazole.
2,2-Dimethyl-2,3,5,6-tetrahydro-7H-3-[[O-[N-methyl-N-(4-tert-butylphenylthiosulfenyl) carbamoyl]oximino]]thiazolo[3,2-a]pyrimidine.
2,2-Dimethyl-3-[O-(carbamoyloximino]-2,3-dihydroimidazo[2,1-b]thiazole.
3-[2,2-Dimethyl-2,3-dihydroimidazo[2,1-b]thiazol-3-ylidenamino-oxycarbonyl methylaminothiosulfenyl methylcarbamoyloxyimino]-2,2-dimethyl 2,3-dihydroimidazo[2,1-b]thiazole.

All compounds within the purview of the above generic formula can be used as insecticidal compounds which exhibit insecticidal activity to a lesser or greater extent. Some of the insecticidal compounds exhibit very powerful insecticidal activity in extremely small dosages while others require larger dosages to be insecticidally effective.

Preferred because of their use as insecticidal compounds which exhibit high levels of insecticidal activity are those of the above generic structural formula wherein:

$R_1 = R_2$ = alkyl most preferably methyl $n = 0, 1$

A = an acyclic alkylene or alkenylene group, or an ortho-substituted phenylene group which forms an unsaturated five, six or seven membered heterocyclic ring which also may contain nitrogen in addition to the two nitrogens, said alkylene, alkenylene, or phenylene ring systems being optionally substituted with one or more $C_1$-$C_4$ alkyl, cyclohexyl, or carbonyl. Most preferably A would constitute part of the following ring systems: pyrimidine, diazepine, triazole, imidazole, triazine and benzimidazole.

$R_3$ and $R_4$ may be the same or different and may be hydrogen, $C_1$-$C_4$ alkyl, $C_1$-$C_4$ alkanoyl, or when $R_3$ is alkyl $R_4$ can be $(S)_y R_5$ wherein:

$y = 1, 2$ $R_5$ = phenyl group unsubstituted or substituted with one or more alkyl groups or a $R_5$ may be a group of the formula:

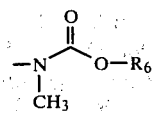

wherein:

$R_6$ is (1) a phenyl compound which may be unsubstituted or substituted with one or more $C_1$-$C_{12}$ alkyl.

(2) a naphthyl group which may be unsubstituted or substituted with one or more alkyl groups, or (3) a group of the formula:

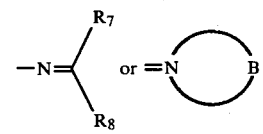

wherein:

$R_7$ is an alkyl group $R_8$ is an alkylthio group.

B is a divalent aliphatic chain completing a five or six membered heterocyclic ring structure, said aliphatic chain having from 2-4 aliphatic carbon atoms, said ring structure may include, in any combination, one or two sulfur, sulfinyl, amino, alkylamino, or carbonyl group.

Some of the preferred compounds are listed by nomenclature and structure as follows.

| Nomenclature | Structure |
|---|---|
| 2,2-Dimethyl-3-[O—(methyl-carbamoyl)oximino]-2,3,5,6-tetrahydro-7H—thiazolo[3,2-a]pyrimidine | |
| 2,2-Dimethyl-3-[O—(methylcarbamoyl)-oximino]-2,3-dihydroimidazo[2,1-b]thiazole | 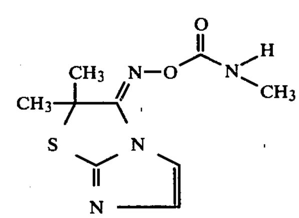 |
| 2,2-Dimethyl-2,3-dihydro-3-[O—[N—methyl-N—(N'—methyl-N'—(1-methylthio-ethylidene aminooxycarbonyl) aminosulfenyl) carbamoyl]oximino]imidazo[2,1-b]thiazole | 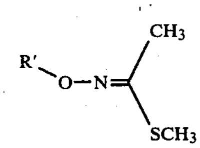 |

-continued

| Nomenclature | Structure |
|---|---|
| 2,2-Dimethyl-2,3-dihydro-3-[O—[N—methyl-N—(N'—methyl-N'—(naphthaleneoxy carbonyl)amino sulfenyl)carbamoyl]oximino]imidazo[2,1-b]thiazole | R'—O-naphthyl |

R' = (structure showing dimethyl group with N—O—C(=O)—N(CH₃)—S—N(CH₃)—C(=O)—CH₃ and imidazo[2,1-b]thiazole ring)

The following specific examples are presented to more particularly illustrate this invention. Examples I—IX show the preparation of the precursor compounds whereas Examples X to XXVII show insecticidal compounds produced from some of the precursor compounds.

EXAMPLE I

Preparation of 2,2-Dimethyl-3-hydroxyimino-2,3,5,6 tetrahydroimidazo[2,1-b]thiazole A 10.2 g (65.4 mmol) of 2-chlorohydroxamoyl chloride was dissolved in 200 ml of methanol and immediately cooled in an ice bath to 0°. To this solution was added 6.68 g (65.4 mmol) of 2-imidazolidinethione in one portion. After the reaction mixture was stirred at 0° for ca. 10 min., 11.09 g (132 mmol) of sodium bicarbonate was added in portions. The reaction mixture was allowed to stir at 25° C. overnight before the solvent was removed in vacuo. The residue was extracted with absolute ethanol and the ethanolic extracts were concentrated in vacuo. The residue was triturated with cold acetonitrilehexane. The insoluble solid (22%) was identified as the desired product:

mp: 188°–191°. nmr (5% DMSO-d6) δ9.75 (br,1, NO$\underline{H}$), 4.10 (brs, 4, —N—CH$_2$CH$_2$N—), 3.50–3.30 (m,4,2 H$_2$O), 1.67 (s,6, gem-dimethyl). ir (CH$_2$Cl$_2$) 3570, 1670, 1620, 1200, 920 cm$^{-1}$.

The following Examples II–IX were prepared in a manner similar to Example I. The nomenclature and structure of the compounds of each example are as follows:

| Example | Nomenclature | Structure |
|---|---|---|
| II | 2,2-Dimethyl-3-hydroxyimino-2,3,5,6-tetrahydro-74-thiazolo[3,2-a]pyrimidine | (structure) |
| III | 2,2,5,5,8,8-Hexamethyl-3-hydroxyimino 2,3,5,6,7,8-hexahydro thiazolo[3,2-a][1,3]diazepine | (structure) |
| IV | 6,6-Dimethyl-5-hydroxyimino-5,6-dihydrothiazolo[2,3-c]1,2,4-triazole | (structure) |
| V | 2,2-Dimethyl-3-hydroxyimino-2,3-dihydroimidazo[2,1-b]thiazole | (structure) |

-continued

| Example | Nomenclature | Structure |
|---|---|---|
| VI | 6,6-Dimethyl-3-hydroxyimino-2,3-dihydrothiazolo[3,2-a]benzimidazole | 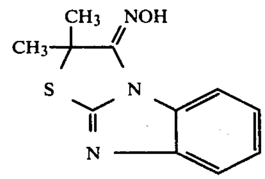 |
| VII | E-2,2-Dimethyl-3-hydroxyimino-7-oxo-2,3-dihydro-7H—thiazolo[3,2-a]pyrimidine | 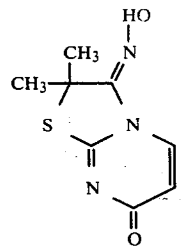 |
| VIII | 2,2-Dimethyl-3-hydroxyimino-5-oxo-2,3-dihydro-5H—thiazolo[3,2-a]pyrimidine | 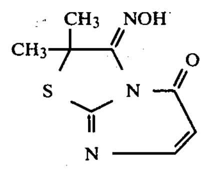 |
| IX | Z-2,2-Dimethyl-3-hydroxyimino-7-oxo-2,3-dihydro-7H—thiazolo[3,2-a]pyrimidine | 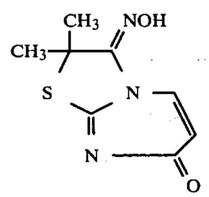 |

The physical data for these compounds are as indicated in Table I.

TABLE I

| Example | MP-°C. | nmr/Anal calcd | Found |
|---|---|---|---|
| II | 191–193° | C 48.22<br>H 6.57<br>N 21.09 | 47.72<br>6.30<br>21.04 |
| III | 161–163° | nmr (5% DMSO-d6) δ<br>1.90–1.50 (m,10,singlet at 1.60 for gem-dimethyl)<br>1.35 (s,6, N>CH₃ CH₃)<br>1.18 (s,6, =N>CH₃ CH₃) | |
| IV | 202–204° | nmr (DMSO-d6) δ<br>12.00 (s,1,NOH)<br>9.20 (s,1,C—H)<br>1.82 (s,6,gem-dimethyl) | |
| V | 202.5–204° | C 45.88<br>H 4.95<br>N 22.93 | C 46.17<br>H 4.83<br>N 23.08 |
| VI | — | nmr (DMSO-d6) δ<br>11.72 (s,1,NOH)<br>8.30–7.10 (m,4, aromatic)<br>1.82 (s,6, gem dimethyl) | |
| VII | >240° | C 45.48<br>H 4.29<br>N 19.88 | C 45.56<br>H 4.20<br>N 20.23 |
| VIII | 132–143° | C 45.48<br>H 4.29<br>N 19.89 | C 45.47<br>H 4.26<br>N 19.99 |

TABLE I-continued

| Example | MP-°C. | nmr/Anal calcd | Found |
|---|---|---|---|
| IX | — | nmr (DMSO-d6) δ<br>12.12 (s,1,OH)<br>8.90 (d,1,CO CH=CH, J = 8 Hz)<br>6.00 (d,1,CO CH=CH, J = 8 Hz)<br>1.78 (s,6, gem-dimethyl) | |

EXAMPLE X

Preparation of 2,2-Dimethyl-3-[O(methylcarbamoyl)oximino]-2,3,5,6-tetrahydroimidazo[2,1-b]thiazole.

To a solution of 2.63 g (14.2 mmol) of 2,2-dimethyl-3-hydroxyimino-2,3,5,6-tetrahydroimidazo [2,1-b]thiazole (I) in 200 ml of a 1:1 mixture of methylene chloride:acetonitrile, taken in a pyrex pressure bottle, was added 1.13 ml (15 mmol) of methylisocyanate and two drops of di-butyltindiacetate. After standing at 25° for 24 hours the solvent was removed in vacuo and the resulting oil was crystallized from hexane/toluene to afford 1.5 g (44%) of the product. mp 142°–147°.

Calc'd for $C_9H_{14}N_4O_2S$: C, 44.61; 4, 5.82; N, 23.12. Found: C, 44.24; 4, 5.81; N, 23.11.

The following examples XI–XVII were prepared in a manner similar to Example X. The nomenclature and structure of the compounds of each example are as follows:

| Example | Nomenclature | Structure |
|---------|--------------|-----------|
| XI | 2,2-Dimethyl-3-[O—(methyl-carbamoyl)oximino]-2,3,5,6-tetrahydro-7H—thiazolo[3,2-a]pyrimidine | 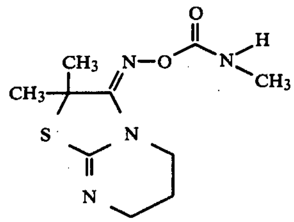 |
| XII | 2,2,5,5,8,8-Hexamethyl-3-[O—(methylcarbamoyl)oximino]-2,3,5,6,7,8-hexahydrothiazolo[3,2-a][1,3]diazepine | 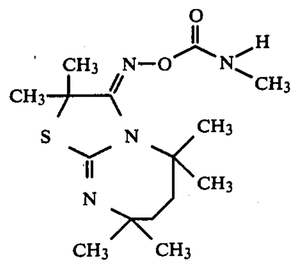 |
| XIII | 6,6-Dimethyl-5-[O—(methylcarbomoyl)-oximino]-5,6-dihydrothiazolo[2,3-c]1,2,4-triazole | 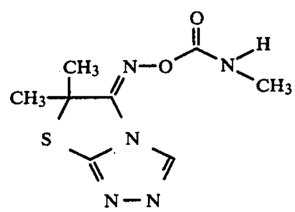 |
| XIV | 2,2-Dimethyl-3-[O—(methylcarbamoyl)-oximino]-2,3-dihydroimidazo[2,1-b]thiazole | 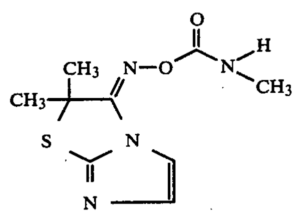 |
| XV | 2,2-Dimethyl-3-[O—(methylcarbamoyl)-oximino]-2,3-dihydrothiazolo[3,2-a]benzimidazole | 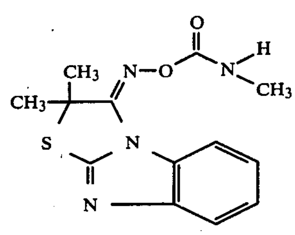 |
| XVI | 2,2-Dimethyl-3-[O—(methylcarbamoyl)-oximino]-7-oxo-2,3-dihydro-7H—thiazolo[3,2-a]pyrimidine | 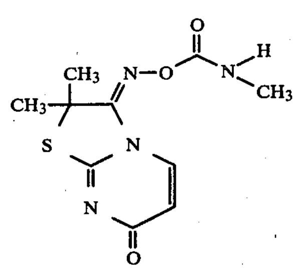 |

-continued

| Example | Nomenclature | Structure |
|---|---|---|
| XVII | 2,2-Dimethyl-6N—cyclohexyl-3-[O—(methylcarbamoyl)oximino] 2,3,5,6-tetrahydro-7H—thiazolo[3,2-a]triazine | 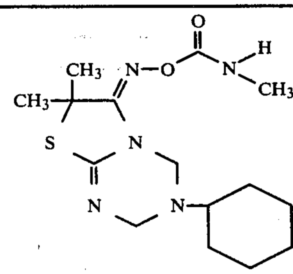 |

The physical data for these compounds are as indicated in Table II.

TABLE II

| Example | MP-°C. | nmr/Anal calcd | Found |
|---|---|---|---|
| XI | 142.5–144° | C 46.85 | C 46.96 |
| | | H 6.29 | H 6.39 |
| | | H 21.86 | N 22.19 |
| XII | 141–143° | C 55.18 | C 55.04 |
| | | H 8.03 | H 8.05 |
| | | N 17.16 | N 17.53 |
| XIII | 167–171° (dec) | C 39.82 | C 39.71 |
| | | H 4.60 | H 4.76 |
| | | N 29.03 | N 26.07 |
| XIV | 133–141° | C 44.98 | C 44.41 |
| | | H 5.04 | H 5.10 |
| | | N 23.32 | N 22.10 |
| XV | 192–195° | C 53.77 | C 53.25 |
| | | H 4.86 | H 4.77 |
| | | N 19.30 | N 19.05 |
| XVI | 146–149° (dec) | C 44.76 | C 43.70 |
| | | H 4.51 | H 5.54 |
| XVII | 158–161° | C 53.07 | C 51.03 |
| | | H 7.42 | H 7.18 |
| | | N 20.63 | N 20.76 |

The following examples XVIII to XXII further illustrate preparation of additional insecticidal compounds with Examples XIX and XXII being prepared in a manner similar to Example XVIII by adding one equivalent of appropriately substituted alcohol or oxime to the bis-(N-alkyl-N-fluorocarbonylamino)sulfide in the presence of an acid acceptor followed by an equivalent of oxime.

The nomenclature and structure of the compounds of each example are as indicated below.

EXAMPLE XVIII

Preparation of
3-[2,2-Dimethyl-2,3-dihydroimidazo[2,1-b]thiazol-3-ylidenamino-oxycarbonyl methylaminosulfenylmethyl carbamoyloxyimino]-2,2-dimethyl 2,3-dihydroimidazo[2,1-b]thiazole A 3.0 g (16.4 mmol) quantity of 2,2-dimethyl-3-hydroxyimino-2,3,5,6-tetrahydroimidazo[2,1-b]thiazole (I) was dissolved in 300 ml of methylene chloride containing 2.28 ml (16.4 mmol) of triethylamine. To this mixture was added 1.5 g (8.2 mmol) of bis-(N-alkyl-N-fluorocarbonylamino)sulfide and the reaction mixture was stirred overnight. The reaction mixture was washed with water (2×200 ml), dried (MgSO4), and concentrated in vacuo to give a solid residue which was recrystallized from ethylacetate. The final product crystallized with one equivalent of solvent (ethylacetate or acetone) per two equivalents of compound. Yield 3.24 g (65%); mp. 177°–180°.

Calcd for [C18H22N8O4S3]2 C4H8O2:C,43.30, H,4.73; N,20.20. Found C,42.82, H,4.70; N,20.1.

| Example | Nomenclature | Structure |
|---|---|---|
| XIX | 2,2-Dimethyl-2,3-dihydro-3-[O—[N—methyl-N—(N'—methyl-N'—(1-methylthio-ethylidene aminooxycarbonyl) aminosulfenyl) carbamoyl]oximino]imidazo[2,1-b]thiazole | 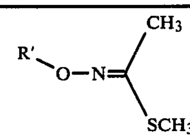 |
| XX | 2,2-Dimethyl-2,3-dihydro-3-[O—[N—methyl-N—(N'—methyl-N'—(naphthalene-oxycarbonyl)amino sulfenyl)-carbamoyl]oximino]imidazo[2,1-b]thiazole | 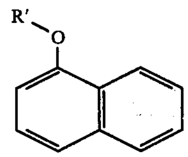 |
| XXI | 2,2-Dimethyl-2,3-dihydro-3-[[O—[N—methyl-N—(N'—methyl-N'—(3,4,5-trimethyl-phenoxycarbonyl) amino sulfenyl)carbamoyl]oximino]]-imidazo[2,1-b]thiazole | 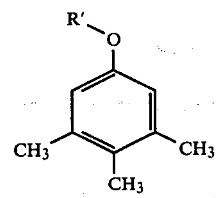 |
| XXII | 2,2-Dimethyl-2,3-dihydro-3-[O—[N—methyl-N—(N'—methyl-N'—(4-n-nonelphen-oxycarbonyl) aminosulfenyl)-carbamoyl]oximino]imnidazo[2,1-b]thiazole | 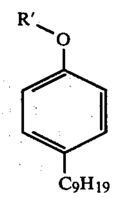 |

TABLE III

| Example | MP | Analysis Calc | Found |
|---|---|---|---|
| XIX | 50–55° | C 38.87 | C 38.19 |
| | | H 4.66 | H 4.83 |
| | | N 19.43 | N 18.56 |
| XX | 85° (dec) | C 53.48 | C 52.91 |
| | | H 4.49 | H 4.65 |

The nomenclature and structure of each example are as indicated below.

TABLE III-continued
Analysis

| Example | Nomenclature | Structure |
|---|---|---|
| XXIV | 2,2-Dimethyl-2,3-dihydro-3-[O—(N—methyl N—pentanoyl-carbamoyl)oximino]-imidazo[2,1-b]thiazole | (Oil) |
| XXV | 2,2-Dimethyl-2,3-dihydro-3-[O—(N—propyl carbamoyl)oximino]-imidazo[2,1-b]thiazole | 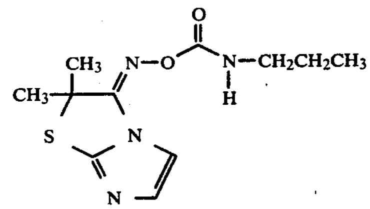 |
| XXVI | 2,2-Dimethyl-2,3-dihydro-3[O—(N—methyl-N—(4-tert-butylphenyl thiosulphenyl)carbamoyl)oximino]-imidazo[2,1-b]thiazole | 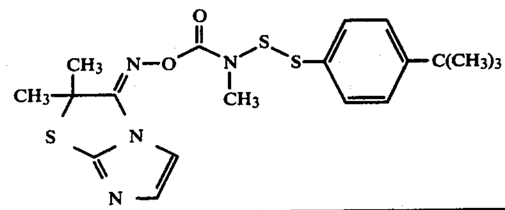 |

| Example | MP | Calc | Found |
|---|---|---|---|
| XXI | 131.5–134° | N 14.85 | N 14.00 |
| | | C 51.81 | C 51.61 |
| | | H 5.44 | H 5.41 |
| XXII | gummy solid | N 15.11 | N 15.09 |
| | | C 57.01 | C 56.64 |
| | | H 6.81 | H 6.86 |
| | | N 12.79 | N 12.60 |

EXAMPLE XXIII

Preparation of 2,2-Dimethyl-2,3-dihydro-3[O-(dimethyl carbamoyl)oximino]-imidazo-[2,1-b]thiazole To a solution of 330 mg (13.6 mmol) of sodium hydride in 150 ml of dry tetrahydrofuran was added 2.50 g (13.6 mmol) of 2,2-dimethyl-3-hydroxyimino-2,3-dihydroimidazo-[2,1-b]thiazole. The reaction mixture was stirred at 25° for 1 hour and cooled in an ice bath before 1.54 g (14.3 mmol) of dimethylcarbamoyl chloride was added. After stirring for 12 hours at 25°, the solvent was removed in vacuo and the residue washed with hexane, dissolved in methylene chloride. The methylene chloride solution was washed with water, dried (MgSO$_4$), and concentrated in vacuo to give 2.94 g (85%) of desired product. m.p. 99°–102.5°.

Anal. Calc'd for C$_{10}$H$_{14}$N$_4$O$_2$S: C, 47.23; H, 5.55; N, 22.03. Found: C, 47.65; H, 5.71; N, 21.89.

The following examples XXIV–XXVI further illustrate preparation of additional insecticidal compounds. Example XXIV was prepared according to the procedure of Example XXIII. Example XV was prepared according to the procedure of Example X and Example XXVI was prepared according to the procedure of Example XVIII.

The physical data for Examples XXIV–XXVI are as indicated in Table IV.

TABLE IV

| Example | MP-°C. | nmr/Anal calcd | Found |
|---|---|---|---|
| XXIV | | C 51.83 | C 51.87 |
| | | H 6.21 | H 6.23 |
| | | N 17.27 | N 16.88 |
| XXV | 103.5–105° | C 49.23 | C 49.26 |
| | | H 6.01 | H 5.96 |
| | | N 20.88 | N 21.13 |
| XXVI | | C 52.26 | C 51.53 |
| | | H 5.54 | H 5.50 |
| | | N 12.83 | N 12.66 |

EXAMPLE XXVII

Preparation of 2,2-Dimethyl-3-[O-(methylcarbamoyl)oximino]-2,3-dihydroimidazo[2,1-b]thiazole-1-oxide A 2.0 g (8.32 mmol) quantity of 2,2-dimethyl-3-[O-(methyl carbamoyl)oximino]-2,3-dihydroimidazo[2,1-b]thiazole was dissolved in 300 ml of ethylacetate. The solution was cooled to −15° before 1.33 g (17.5 mmol) of peracetic acid was added. The reaction mixture was allowed to warm to 25° and stirred for 1 d, followed by concentration to ca. 100 ml and placing in the freezer overnight. The precipitate was collected to give 1.5 g (70%) of product. m.p. 147.5°–149°.

Anal. calc'd for C$_9$H$_{12}$N$_4$O$_3$S: C, 42.18; H, 4.72; N, 21.86. Found: C, 41.91; H, 4.75; N, 21.65.

Selected new compounds were evaluated to determine their pesticidal activity against mites, nematodes, and certain insects, including an aphid, a caterpillar, a beetle and a fly.

Suspensions of the test compounds were prepared by dissolving one gram of compound in 50 milliliters of acetone in which had been dissolved 0.1 gram (10 percent of the weight of compound) of an alkylaryl polyether alcohol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The concentrations in parts per million by weight employed in the tests described below were obtained by appropriate dilutions of the stock suspension with water. The test procedures were as follows:

Adults and nymphal stages of the bean aphid (*Aphis fabae* Scop.) reared on potted dwarf nasturtium plants at 65°–70° F. and 50±5 percent relative humidity, constituted with test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. aphids remaining on the plants were observed closely for movement and those which were unable to move the length of the body upon stimulation by prodding were considered dead.

Larvae of the southern armyworm (Spodopteraeridania, (Cram.)), reared on Tendergreen bean plants at a temperature of 80°±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°–85° F. for three days. Although the larvae could easily consume the whole leaf within twenty-four hours, no more food was added. Larvae which were unable to move the length of the body, even upon stimulation by prodding, were considered dead.

Fourth instar larvae of the Mexican bean beetle (*Epilachna varivestis*, Muls.), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100–110 milliliters of test compound formulation by use of a DeVilbiss spray gun set at 10 psig air pressure. This application, which lasted 25 seconds, was sufficient to wet plants to run-off. As a control, 100–110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F. for three days. Although the larvae could easily consume the leaf within 24 to 48 hours, no more food was added. Larvae which were unable to move the length of the body, even upon stimulation, were considered dead.

Four to six day old adult house flies (*Musca domestica*, L.), reared according to the specifications of the Chemical Specialties Manufacturing Association (Blue Book, McNair-Dorland Co., N.Y. 1954; pages 243–244, 261) under controlled conditions of 80°±5° F. and 50±5 percent relative humidity, were the test insects. The flies were immobilized by anesthetizing with carbon dioxide and twenty five immobilized individuals, males and females, were transferred to a cage consisting of a standard food strainer about five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a soufflé cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 percent. Flies which showed no sign of movement on prodding were considered dead.

Adults and nymphal stages of the two-spotted mite (*Tetranychus urticae* Koch), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty-four hours. Following the twenty-four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of water solution containing acetone and emulsifier in the same concentration as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

The results of these tests are set forth in Table III below. In these tests the pesticidal activity of the compounds at the indicated dosage rate against aphid, mite, Southern Armyworm, Bean Beetle and house fly was rated as follows:
A = excellent control
B = partial control
C = no control those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the aid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, amphoteric or cationic dispersing and emulsifying agents may be employed; for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will

TABLE IV

| | | | Biological Data | | | | |
|---|---|---|---|---|---|---|---|
| Example | Bean Aphid | Mite Adult | Southern Armyworm Larvae | Southern Armyworm Egg | Mexican Bean Beetle | House Fly | Nematode |
| I | C | C | C | C | C | C | C |
| VII | C | C | C | C | C | C | C |
| X | A | A | C | A | A | A | C |
| XI | A | A | A | A | A | A | C |
| XII | A | C | C | C | C | B | C |
| XIII | A | B | B | C | A | A | B |
| XIV | A | A | A | A | A | A | C |
| XV | B | C | C | C | C | C | C |
| XVI | C | C | B | C | C | C | C |
| XVII | C | C | B | C | C | A | B |
| XVIII | A | A | A | A | A | A | C |
| XIX | A | A | A | A | A | A | C |
| XX | A | A | A | A | A | A | C |
| XXI | A | A | A | A | A | A | C |
| XXII | B | C | A | C | A | A | C |
| XXIII | A | A | A | C | A | A | C |
| XXIV | A | A | A | C | A | A | — |
| XXV | A | A | A | B | A | A | C |
| XXVI | A | A | A | C | A | A | C |
| XXVII | A | A | A | C | A | A | A |

It will be understood that the plant species employed in the above tests are merely representative of a wide variety of plant pest that can be controlled by the use of the compounds of this invention. The compounds contemplated in this invention may be applied as mite ovicides and miticides according to methods known to usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultraviolet light, oxidation, or hydrolysis in the presence of moisture or, at least such decomposition, oxidation, and hydrolysis as would materially decrease the desirable pesticidal characteristic of the toxicants or impart undesirable characteristic for instance, phytotoxicity, to the toxicants. The toxicants are so chemically inert that they are compatible with substantially any other constituents of the spray schedule, and they may be used in the soil, upon the seeds, or the roots of plants without injuring either the seeds or roots of plants. They may also be used in combination with other pesticidally active compounds. When used as miticides they will normally be applied to the foliage of the plants to be treated. It will be appreciated that the compounds of this invention can also be used in combination with other biologically active compounds.

What is claimed is:

1. Compounds of the formula:

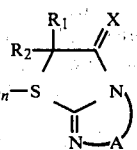

wherein
R$_1$ and R$_2$ are the same or different and are individually hydrogen, C$_1$-C$_6$ alkyl or halogen;
n=0, 1 or 2;

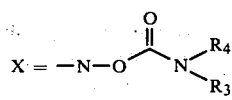

including E and Z isomers;
A is an acyclic, cyclic, or bicyclic alkylene or alkenylene group, or an ortho-substituted phenylene group which forms an unsaturated five membered heterocyclic ring which can also have nitrogen, or carbonyl in addition to the two nitrogens, said alkylene, alkenylene, or phenylene ring systems being optionally substituted with one or two C$_1$-C$_4$ alkyl, cyclohexyl, alkoxy, phenoxy, alkylthio, halogen, amido, alkylamido, nitrile or nitro groups;
R$_3$ and R$_4$ may be the same or different and are individually hydrogen, C$_1$-C$_4$ alkyl or C$_1$-C$_4$ alkanoyl which can be substituted with one or two halogens and in the case when R$_3$ is alkyl R$_4$ can also be —(S)$_y$—R$_5$ wherein:
y=1 or 2;
R$_5$=(a) C$_1$-C$_18$ alkyl, C$_3$-C$_8$ cycloalkyl or perhaloalkyl;

(b) dialkyl amino or pyrrolidino group each of which may be unsubstituted or substituted with one or two alkyl groups; or
(c) a phenyl group which may be unsubstituted or substituted with one or two alkyl, chloro, fluoro, cyano, nitro, alkoxy, trifluoromethyl, alkylthio, alkylsulfinyl, alkylsulfonyl, alkoxyalkyl, alkylthioalkyl, alkylsulfinylalkyl, alkylsulfonylalkyl, or dialkylamino: or
(d) a group of the formula:

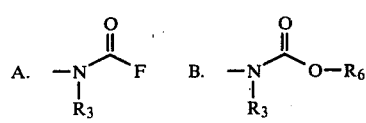

wherein:
R$_6$ is
(1) C$_1$-C$_{12}$ alkyl, alkoxyalkyl, or a phenylalkyl group; or
(2) a phenyl group which may be unsubstituted or substituted with one or two C$_1$-C$_{12}$ alkyl, chloro, fluoro, alkoxy, alkylthio, alkylthioalkyl, alkylsulfinyl, alkylsulfinylalkyl, alkylsulfonyl, alkylsulfonylalkyl, alkynyloxy, dialkylamino, alkoxyimino, formamidino, cyano, dioxolanyl, or dithiolanyl groups in any combination; or
(3) a naphthyl, tetrahydronaphthyl, dihydrobenzofuranyl, benzodioxolanyl, or benzothienyl group all of which may be unsubstituted or substituted with one or two alkyl groups; or
(4) a group of the formula

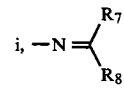

wherein:
R$_7$ is chloro, alkyl, alkoxy, alkylthio, cyanoalkylthio, amidoalkylthio or cyano group; or R$_7$ is hydrogen provided R$_8$ is not hydrogen;
R$_8$ is an alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, haloalkyl, or phenyl group; said phenyl group may contain one or two alkyl, chloro, or fluoro groups in any combination; or R$_8$ is hydrogen provided R$_7$ is not hydrogen;
with the proviso that when R$_6$ is a phenyl group substituted with an alkyl group, no single alkyl or alkylene moiety in any R$_5$, R$_6$, R$_7$, or R$_8$ group can include more than eight carbon atoms except where indicated.

2. A compound according to claim 1 wherein:
R$_1$ and R$_2$ are both alkyl
n=0, or 1
A is an acyclic alkylene or alkenylene group, or an ortho-substituted phenylene group which forms an unsaturated five membered heterocyclic ring which also may have nitrogen or carbonyl in addition to the two nitrogens, said alkylene, alkenylene, or phenylene ring systems being optionally substituted with one or two C$_1$-C$_4$ alkyl or cyclohexyl.

3. A compound according to claim 2 wherein R$_1$ and R$_2$ are both methyl.

4. Compounds of the formula:

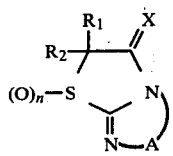

wherein:
$R_1$ and $R_2$ are both alkyl
$n = 0$ or 1

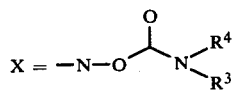

A is an acyclic alkylene or alkenylene group, or an ortho-substituted phenylene group which forms an unsaturated five membered heterocyclic ring which also may have nitrogen or carbonyl in addition to the two nitrogens, said alkylene, alkenylene, or phenylene ring systems being optionally substituted with one or two $C_1$-$C_4$ alkyl or cyclohexyl $R_3$ and $R_4$ may be the same or different and may be hydrogen, $C_1$-$C_4$ alkyl, $C_1$-$C_4$ alkanoyl, or when $R_3$ is alkyl $R_4$ can be $(S)_y R_5$ wherein:
$y = 1, 2$ $R_5$ = phenyl group unsubstituted or substituted with one or two alkyl groups or a $R_5$ may be a group of the formula:

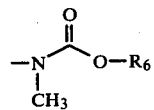

wherein:
$R_6$ is (1) a phenyl compound which may be unsubstituted or substituted with one or two $C_1$-$C_{12}$ alkyl.
(2) a naphthyl group which may be unsubstituted or substituted with one or two alkyl groups, or
(3) a group of the formula:

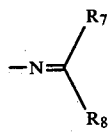

wherein:
$R_7$ is an alkyl group
$R_8$ is an alkylthio group.

5. A compound according to claim 4 wherein $R_1$ and $R_2$ are methyl.

6. 2,2-Dimethyl-3-[O-(methylcarbamoyl)oximino]-2,3-dihydroimidazo[2,1-b]thiazole.

7. 2,2-Dimethyl-2,3-dihydro-3-[O-[N-methyl-N-(N'-methyl-N'-(1-methylthio-ethylidene aminooxycarbonyl)aminosulfenyl)carbamoyl]oximino]imidazo [2,1-b]thiazole.

8. 2,2-Dimethyl-2,3-dihydro-3-[O-[N-methyl-N-(N'-methyl-N'-methyl-N'-(naphthaleneoxy carbonyl-)aminosulfenyl)carbamoyl]oximino]imidazo[2,1-b]thiazole.

9. A miticidal and insecticidal composition comprising an acceptable carrier and as an active toxicant a miticidally or insecticidally effective amount of a compound of the formula:

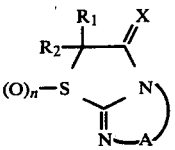

wherein
$R_1$ and $R_2$ are the same or different and are individually hydrogen, $C_1$-$C_6$ alkyl or halogen;
$n = 0, 1$ or 2;

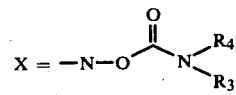

including E and Z isomers;
A is an acyclic, cyclic, or bicyclic alkylene or alkenylene group, or an ortho-substituted phenylene group which forms an unsaturated five membered heterocyclic ring which can also have nitrogen, or carbonyl in addition to the two nitrogens, said alkylene, alkenylene, or phenylene ring systems being optionally substituted with one or two $C_1$-$C_4$ alkyl, cyclohexyl, alkoxy, phenoxy, alkylthio, halogen, amido, alkylamido, nitrile or nitro groups;

$R_3$ and $R_4$ may be the same or different and are individually hydrogen, $C_1$-$C_4$ alkyl or $C_1$-$C_4$ alkanoyl which can be substituted with one or two halogens and in the case when $R_3$ is alkyl $R_4$ can also be —$(S)_y$—$R_5$ wherein:
$y = 1$ or 2;
$R_5 =$ (a) $C_1$-$C_{18}$ alkyl, $C_3$-$C_8$ cycloalkyl or perhaloalkyl;
(b) dialkyl amino amino, pyrrolidino group each of which may be unsubstituted or substituted with one or two alkyl groups; or
(c) a phenyl group which may be unsubstituted or substituted with one or two alkyl, chloro, fluoro, cyano, nitro, alkoxy, trifluoromethyl, alkylthio, alkylsulfinyl, alkylsulfonyl, alkoxyalkyl, alkylthioalkyl, alkylsulfinylalkyl, alkylsulfonylalkyl, or dialkylamino: or
(d) a group of the formula:

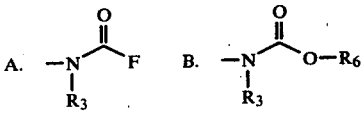

wherein:
$R_6$ is:
(1) $C_1$-$C_{12}$ alkyl, alkoxyalkyl, or a phenylalkyl group; or
(2) a phenyl group which may be unsubstituted or substituted with one or two $C_1$-$C_{12}$ alkyl, chloro, fluoro, alkoxy, alkylthio, alkylthioalkyl, alkylsulfinyl, alkylsulfinylalkyl, alkylsulfonyl, alkyl sulfonylalkyl, alkynyloxy, dialkylamino, alkoxy imino, formamidino, cyano, dioxolanyl, or dithiolanyl groups in any combination; or (3) a naphthyl, tetrahydronaphthyl, dihydrobenzofuranyl, benzodioxolanyl, or benzothienyl group all of which may be unsubstituted or substituted with one or two alkyl groups; or (4) a group of the formula $$\text{i, } -N=\begin{matrix} R_7 \\ R_8 \end{matrix}$$

wherein:

$R_7$ is chloro, alkyl, alkoxy, alkylthio, cyanoalkylthio, amidoalkylthio or cyano group; or $R_7$ is hydrogen provided $R_8$ is not hydrogen;

$R_8$ is an alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, haloalkyl, or phenyl group; said phenyl group may have one or two alkyl, chloro, or fluoro groups in any combination; or $R_8$ is hydrogen provided $R_7$ is not hydrogen;

with the proviso that when $R_6$ is a phenyl group substituted with an alkyl group, no single alkyl or alkylene moiety in any $R_5$, $R_6$, $R_7$, or $R_8$ group can include more than eight carbon atoms except where indicated.

10. A composition according to claim 9 wherein:
$R_1$ and $R_2$ are both alkyl
$n=0$, or 1
A is an acyclic alkylene or alkenylene group, or an ortho-substituted phenylene group which forms an unsaturated five membered heterocyclic ring which also may have nitrogen or carbonyl in addition to the two nitrogens, said alkylene, alkenylene, or phenylene ring systems being optionally substituted with one or two $C_1$–$C_4$ alkyl or cyclohexyl.

11. A composition according to claim 10 wherein $R_1$ and $R_2$ are both methyl.

12. A miticidal and insecticidal composition comprising an acceptable carrier and as an active toxicant a miticidally or insecticidally effective amount of a compound of the formula:

wherein:
$R_1$ and $R_2$ are both alkyl
$n=0$ or 1

$$X = -N-O\overset{O}{\underset{}{\|}}C\begin{matrix} R_4 \\ N \\ R_3 \end{matrix}$$

alkenylene group, or an ortho-substituted phenylene group which forms an unsaturated five membered heterocyclic ring which also may have nitrogen or carbonyl in addition to the two nitrogens, said alkylene, alkenylene, or phenylene ring systems being optionally substituted with one or two $C_1$–$C_4$ alkyl or cyclohexyl.

$R_3$ and $R_4$ may be the same or different and may be hydrogen, $C_1$–$C_4$ alkyl, $C_1$–$C_4$ alkanoyl, or when $R_3$ is alkyl $R_4$ can be $(S)_yR_5$ wherein:
$y=1,2$
$R_5$ = phenyl group unsubstituted or substituted with one or two alkyl groups or a $R_5$ may be a group of the formula:

$$-N\underset{CH_3}{|}\overset{O}{\underset{}{\|}}C-O-R_6$$

wherein:
$R_6$ is (1) a phenyl compound which may be unsubstituted or substituted with one or two $C_1$–$C_{12}$ alkyl.
(2) a naphthyl group which may be unsubstituted or substituted with one or two alkyl groups, or
(3) a group of the formula:

$$-N=\begin{matrix} R_7 \\ R_8 \end{matrix}$$

wherein:
$R_7$ is an alkyl group
$R_8$ is an alkylthio group.

13. A composition according to claim 12 wherein $R_1$ and $R_2$ are methyl.

14. A composition according to claim 9 wherein the active toxicant is 2,2-Dimethyl-3-[O-methylcarbamoyl)-oximino]-2,3-dihydroimidazo[2,1-b]thiazole.

15. A composition according to claim 9 wherein the active toxicant is 2,2-Dimethyl-2,3-dihydro-3-[O-[N-methyl-N-(N'-methyl-N'-(1-methylthio-ethylidene aminooxycarbonyl)aminosulfenyl)carbamoyl]oximino]imidazo[2,1-b]thiazole.

16. A composition according to claim 9 wherein the active toxicant is 2,2-Dimethyl-2,3-dihydro-3-[O-[N-methyl-N-(N'-methyl-N'-(naphthaleneoxy carbonyl)aminosulfenyl)carbamoyl]oximino]imidazo[2,1-b]thiazole.

17. A method of controlling insects which comprises subjecting them to an insecticidally effective amount of a compound of the formula:

wherein
$R_1$ and $R_2$ are the same or different and are individually hydrogen, $C_1$–$C_6$ alkyl or halogen;
$n=0$, 1 or 2;

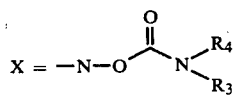

including E and Z isomers;

A is an acyclic, cyclic, or bicyclic alkylene or alkenylene group, or an ortho-substituted phenylene group which forms an unsaturated five membered heterocyclic ring which can also have nitrogen, or carbonyl in addition to the two nitrogens, said alkylene, alkenylene, or phenylene ring systems being optionally substituted with one or two $C_1$–$C_4$ alkyl, cyclohexyl, alkoxy, phenoxy, alkylthio, halogen, amido, alkylamido, nitrile, or nitro groups;

$R_3$ and $R_4$ may be the same or different and are individually hydrogen, $C_1$–$C_4$ alkyl or $C_1$–$C_4$ alkanoyl which can be substituted with one or two halogens and in the case when $R_3$ is alkyl $R_4$ can also be —$(S)_y$—$R_5$ wherein:

y = 1 or 2;

$R_5$ = (a) $C_1$–$C_{18}$ alkyl, $C_3$–$C_8$ cycloalkyl or perhaloalkyl;

(b) dialkyl amino or pyrrolidino group each of which may be unsubstituted or substituted with one or two alkyl groups; or (c) a phenyl group which may be unsubstituted or substituted with one or two alkyl, chloro, fluoro, cyano, nitro, alkoxy, trifluoromethyl, alkylthio, alkylsulfinyl, alkylsulfonyl, alkoxyalkyl, alkylthioalkyl, alkylsulfinylalkyl, alkylsulfonylalkyl, or dialkylamino: or (d) a group of the formula:

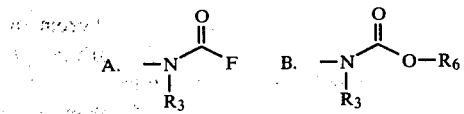

wherein:

$R_6$ is:

(1) $C_1$–$C_{12}$ alkyl, alkoxyalkyl, or a phenylalkyl group; or (2) a phenyl group which may be unsubstituted or substituted with one or two $C_1$–$C_{12}$ alkyl, chloro, fluoro, alkoxy, alkylthio, alkylthioalkyl, alkylsulfinyl, alkylsulfinylalkyl, alkylsulfonyl, alkylsulfonylalkyl, alkynyloxy, dialkylamino, alkoxy imino, formamidino, cyano, dioxolanyl, or dithiolanyl groups in any combination; or (3) a naphthyl, tetrahydronaphthyl, dihydrobenzofuranyl, benzodioxolanyl, or benzothienyl group all of which may be unsubstituted or substituted with one or two alkyl groups; or (4) a group of the formula

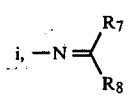

wherein:

$R_7$ is chloro, alkyl, alkoxy, alkylthio, cycanoalkylthio, amidoalkylthio or cyano group; or $R_7$ is hydrogen provided $R_8$ is not hydrogen;

$R_8$ is an alkyl, alkylthio, alkoxycarbonyl, aminocarbonyl, alkylaminocarbonyl, dialkylaminocarbonyl, alkylthioalkyl, cyanoalkyl, alkylsulfinylalkyl, alkylsulfonylalkyl, alkoxyalkyl, nitroalkyl, hydroxyalkyl, haloalkyl, or phenyl group; said phenyl group may have one or two alkyl, chloro, or fluoro groups in any combination; or $R_8$ is hydrogen provided $R_7$ is not hydrogen;

with the proviso that when $R_6$ is a phenyl group substituted with an alkyl group, no single alkyl or alkylene moiety in any $R_5$, $R_6$, $R_7$, or $R_8$ group can include more than eight carbon atoms except where indicated.

18. A method according to claim 17 wherein:

$R_1$ and $R_2$ are both alkyl n = 0, or 1

A is an acyclic alkylene or alkenylene group, or an ortho-substituted phenylene group which forms an unsaturated five membered heterocyclic ring which also may have nitrogen or carbonyl in addition to the two nitrogens, said alkylene, alkenylene, or phenylene ring systems being optionally substituted with one or two $C_1$–$C_4$ alkyl or cyclohexyl.

19. A method according to claim 18 wherein $R_1$ and $R_2$ are both methyl.

20. A method of controlling insects which comprises subjecting them to an insecticidally effective amount of a compound of the formula:

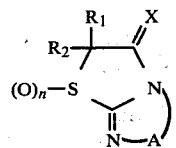

wherein:

$R_1$ and $R_2$ are both alkyl n = 0 or 1

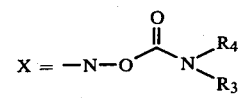

A is an acyclic alkylene or alkenylene group, or an ortho-substituted phenylene group which forms an unsaturated five member heterocyclic ring which also may have nitrogen or carbonyl in addition to the two nitrogens, said alkylene, alkylene, or phenylene ring systems being optionally substituted with one or two $C_1$–$C_4$ alkyl or cyclohexyl.

$R_3$ and $R_4$ may be the same or different and may be hydrogen, $C_1$–$C_4$ alkyl, $C_1$–$C_4$ alkanoyl, or when $R_3$ is alkyl $R_4$ can be $(S)_y R_5$ wherein:

y = 1, 2

$R_5$—phenyl group unsubstituted or substituted with one or more alkyl groups or a $R_5$ may be a group of the formula:

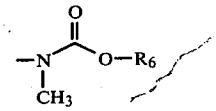

wherein:

R₆ is (1) a phenyl compound which may be unsubstituted or substituted with one or two $C_1$–$C_{12}$ alkyl.
(2) a naphthyl group which may be unsubstituted or substituted with one or two alkyl groups, or
(3) a group of the formula:

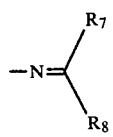

wherein:
R₇ is an alkyl group
R₈ is an alkylthio group.

21. A method according to claim 20 wherein R₁ and R₂ are methyl.

22. A method according to claim 17 wherein the compound is 2,2-Dimethyl-3-[O-(methylcarbamoyl)-oximino]-2,3-dihydroimidazo[2,1-b]thiazole.

23. A method according to claim 17 wherein the compound is 2,2-Dimethyl-2,3-dihydro-3-[O-[N-methyl-N-(N'-methyl-N'-(1-methylthio-ethylidene aminooxycarbonyl)aminosulfenyl)carbamoyl]oximino]imidazo[2,1-b]thiazole.

24. A method according to claim 17 wherein the compound is 2,2-Dimethyl-2,3-dihydro-3-[O-[N-methyl-N-(N'-methyl-N'-(naphthaleneoxy carbonyl)aminosulfenyl)carbamoyl]oximino]imidazo[2,1-b]thiazole.

25. A compound according to claim 4 wherein A when taken with the nitrogen atoms to which it is attached is selected from the group of triazole, imidazole and benzimidazole.

26. A compound according to claim 12 wherein A when taken with the nitrogen atoms to which it is attached is selected from the group of triazole, imidazole and benzimidazole.

27. A method according to claim 20 wherein A when taken with the nitrogen atoms to which it is attached is selected from the group of triazole, imidazole and benzimidazole.

* * * * *